(12) United States Patent
Halsmer et al.

(10) Patent No.: US 6,898,269 B2
(45) Date of Patent: May 24, 2005

(54) METHODS AND APPARATUS FOR X-RAY IMAGES

(75) Inventors: Matthew Aaron Halsmer, Waukesha, WI (US); Jonathan Carl Boomgaarden, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 164 days.

(21) Appl. No.: 10/248,698

(22) Filed: Feb. 10, 2003

(65) Prior Publication Data

US 2004/0156476 A1 Aug. 12, 2004

(51) Int. Cl.⁷ .................................................. G21K 5/10
(52) U.S. Cl. ...................................... 378/146; 378/145
(58) Field of Search .............................. 378/22, 24, 25, 378/26, 57, 86, 87, 88, 90, 145, 146, 147, 151, 155

(56) References Cited

U.S. PATENT DOCUMENTS

| | | | | |
|---|---|---|---|---|
| 4,097,748 A | * | 6/1978 | Monvoisin ................... | 378/146 |
| 4,361,899 A | * | 11/1982 | Amplatz ....................... | 378/21 |
| 4,490,835 A | * | 12/1984 | Wons ........................... | 378/146 |
| 4,651,337 A | | 3/1987 | Boomgaarden et al. | |
| 4,675,893 A | * | 6/1987 | Duinker et al. ............. | 378/151 |
| 4,991,189 A | | 2/1991 | Boomgaarden et al. | |
| 5,204,783 A | | 4/1993 | Buss et al. | |
| 5,291,539 A | | 3/1994 | Thumann et al. | |
| 5,481,586 A | * | 1/1996 | Coe ........................... | 378/146 |
| 5,485,500 A | | 1/1996 | Baba et al. | |
| 5,600,701 A | | 2/1997 | Baba et al. | |
| 5,617,465 A | * | 4/1997 | Bucher ....................... | 378/146 |
| 5,712,890 A | * | 1/1998 | Spivey et al. ................. | 378/37 |
| 6,339,636 B1 | * | 1/2002 | Ogawa ....................... | 378/146 |
| 6,422,749 B1 | | 7/2002 | Polkus et al. | |
| 6,618,465 B2 | * | 9/2003 | Mohr et al. ................... | 378/58 |
| 6,621,888 B2 | * | 9/2003 | Grodzins et al. ............. | 378/57 |
| 6,647,092 B2 | * | 11/2003 | Eberhard et al. ............. | 378/65 |

* cited by examiner

*Primary Examiner*—Allen C. Ho
(74) *Attorney, Agent, or Firm*—Carl B. Horton, Esq.; Armstrong Teasdale LLP

(57) ABSTRACT

A method for producing an image in a x-ray imaging system is provided. The x-ray imaging system includes an x-ray source which projects an x-ray beam collimated by a collimation assembly to pass through an object and impinge on an x-ray receptor to produce the image. The method includes rotating the collimation assembly about a focal point while the x-ray source is substantially fixed and producing x-rays. The method further includes adjusting the position of the x-ray receptor during rotation of the collimation assembly to receive the x-ray beam.

24 Claims, 3 Drawing Sheets

METHODS AND APPARATUS FOR X-RAY IMAGES

BACKGROUND OF INVENTION

This invention relates generally to x-ray diagnostic medical imaging and, more particularly, to methods and apparatus for x-ray images.

In many x-ray imaging system configurations, an x-ray source projects an area beam which is collimated to pass through a region of interest of the object being imaged, such as a patient. The beam, after being attenuated by the object, impinges upon an array of radiation detectors. The intensity of the radiation beam received at the detector array is dependent upon the attenuation of the x-ray beam by the object. In a digital detector, each detector element, or pixel, of the array produces a separate electrical signal that is a measurement of the beam attenuation at that location of the detector. The attenuation measurements from all the detector pixels are acquired separately to produce a transmission profile.

In a typical x-ray imaging system, a patient is positioned between an x-ray tube and an image receptor having a planar imaging surface, such as an x-ray film or a digital solid state detector. The tube projects a beam of x-radiation toward the detector surface and through the body structure of the patient to be imaged. The area of projected radiation, which is incident on the detector, defines the active imaging area (AIA). Generally, the x-ray beam field, or field of view (FOV), which is defined herein to be the intersection of the projected beam and the detector plane, must be coincident with, or lie within, the boundaries of the detector surface in order to avoid loss of image data. The FOV may be adjusted by rotating or tilting the tube to vary the direction of the projected x-ray beam, and also by operating a collimator to vary the width and length dimensions of the x-ray beam. Further adjustments may be made by linear translation of the tube and/or the detector Combining adjacent images to achieve an image longer than the length of the detector requires some movement on the part of the x-ray source between exposures. Due to the length of an exposure, the images are subject to distortion or blurring from motion of the source during exposure as well as vibrations of the source if the unit is stopped, both resulting in lower image quality. In addition, pasting adjacent images typically requires some overlap, which results in extra dose to the patient at some positions. Also, because of overlap at this region, there is a different signal to noise ratio in this region than in the rest of the image which can be seen as bands of high resolution on the final image.

SUMMARY OF INVENTION

In one aspect, a method for producing an image in a x-ray imaging system is provided. The x-ray imaging system includes an x-ray source which projects an x-ray beam collimated by a collimation assembly to pass through an object and impinge on an x-ray receptor to produce the image. The method includes rotating the collimation assembly about a focal point while the x-ray source is substantially fixed and producing x-rays. The method further includes adjusting the position of the x-ray receptor during rotation of the collimation assembly to receive the x-ray beam.

In another aspect, an x-ray imaging system is provided. The x-ray imaging system includes an x-ray source for producing an x-ray beam, and a collimated assembly for collimating the x-ray beam to pass through an object. The x-ray imaging system further includes an x-ray receptor and a computer operationally coupled to the collimation assembly and x-ray receptor. The computer is configured to rotate the collimation assembly about a focal point while the x-ray source is substantially fixed and producing x-rays.

In another aspect, a method for producing an image in a medical x-ray imaging system is provided. The medical x-ray imaging system includes an x-ray source which projects an x-ray beam collimated by a collimation assembly to pass through an object and impinge on an x-ray receptor to produce the image. The method includes rotating the collimation assembly about a focal point while the x-ray source is substantially fixed and producing x-rays. The method further includes adjusting the position of the x-ray receptor during rotation of the collimation assembly to receive the x-ray beam.

In another aspect, a computer is provided. The computer is configured to rotate a collimation assembly about a focal point while an X-ray source is substantially fixed and producing x-rays. The X-ray source projects an X-ray beam collimated by the collimation assembly to pass through an object and impinge on an X-ray receptor to produce a plurality of images. The computer is further configured to adjust the position of the X-ray receptor to receive the X-ray beam in a plurality of positions.

In a further aspect, a computer readable medium embedded with a program configured to instruct a computer is provided. The computer readable medium is configured to instruct the computer to rotate a collimation assembly about a focal point while an X-ray source is substantially fixed and producing x-rays. The X-ray source projects an X-ray beam collimated by the collimation assembly to pass through an object and impinge on an X-ray receptor to produce a plurality of images. The computer readable medium is further configured to instruct the computer to adjust the position of the X-ray receptor to receive the X-ray beam in a plurality of positions.

DETAILED DESCRIPTION

Figure 1:
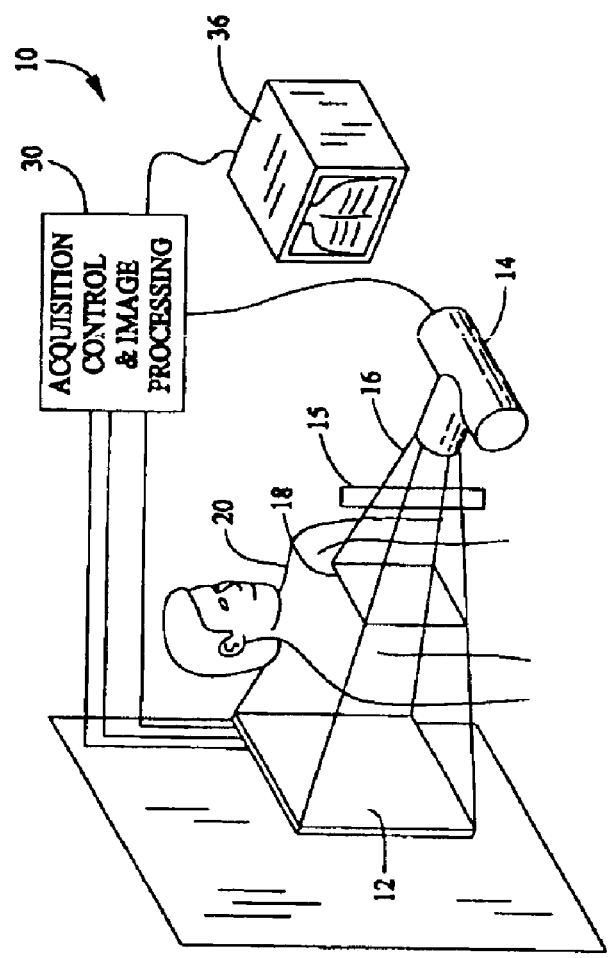
FIG. 1 is a perspective view of an imaging system.

FIG. 1 is a perspective view of an imaging system 10, for example, an x-ray imaging system, is shown as including a receptor or detector array 12 and an x-ray source 14 collimated by a collimator 15 to provide an area x-ray beam 16 passing through an area 18 of a patient 20. Detector array 12 is comprised of a number of detector elements (not shown), organized within the imaging plane, which together detect the projected image produced by the attenuated transmission of x-rays through imaged patient 20. Beam 16 is attenuated by an internal structure (not shown) of patient 20 to then be received by detector array 12, which extends generally over an area in a plane perpendicular to the axis of x-ray beam 16.

System 10 also includes an acquisition control and image processing circuit 30, which is electrically connected to x-ray source 14 and detector array 12. More specifically, circuit 30 controls x-ray source 14, turning it on and off and controlling the tube current and thus the fluence of x-rays in beam 16 and/or the tube voltage and thereby altering the energy of the x-rays in beam 16. In one embodiment, acquisition control and image processing circuit 30 includes a data acquisition system (DAS) having at least one DAS module, or circuit (not shown in FIG. 1), which samples data from detector array 12 and transmits the data signals for subsequent processing. In one embodiment, each DAS module includes a plurality of driver channels or a plurality of read out channels. Acquisition control and image processing circuit 30 receives sampled x-ray data from DAS and generates an image and displays the image on a monitor, or cathode ray tube display 36 based on the data provided by each pixel.

In one embodiment, circuit 30 is a computer including a device, for example, a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, a CD-ROM, a DVD or an other digital source such as a network or the Internet, as well as yet to be developed digital means. In another embodiment, the computer executes instructions stored in firmware (not shown). The computer is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Figure 2:
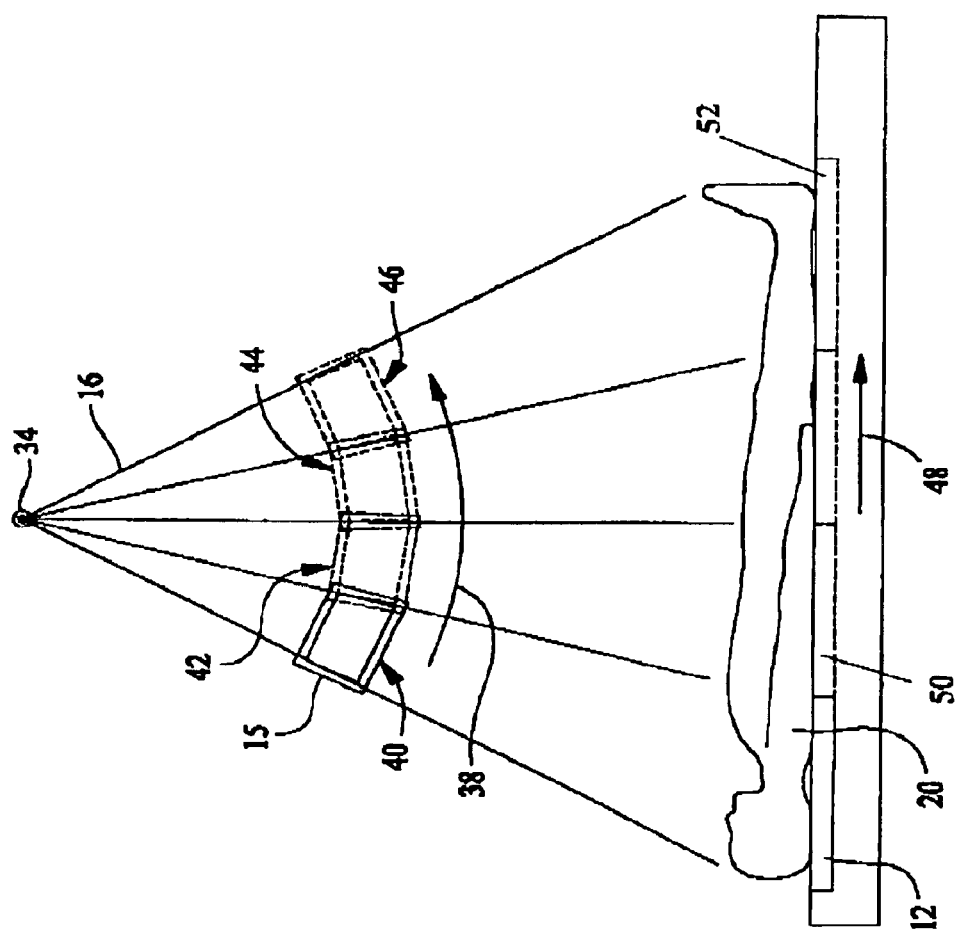
FIG. 2 is an illustration of a collimator assembly for use with the imaging system of FIG. 1.

FIG. 2 is an illustration of collimator assembly 15 rotating about focal point 34, represented by arrow 38, while x-ray source 14 is substantially fixed to produce a plurality of images. Uncollimated x-rays 16 radiating from a focal point 34 in x-ray source 14 (not shown in FIG. 2) are collimated by collimator assembly 15. Collimator assembly 15 is shown in positions 40, 42, 44, and 46 but rotates through a plurality of positions intermediate positions 40, 42, 44, and 46. Detector array 12 adjusts, represented by arrow 48, during rotation of collimator assembly 15 in a plurality of positions.

Figure 3:
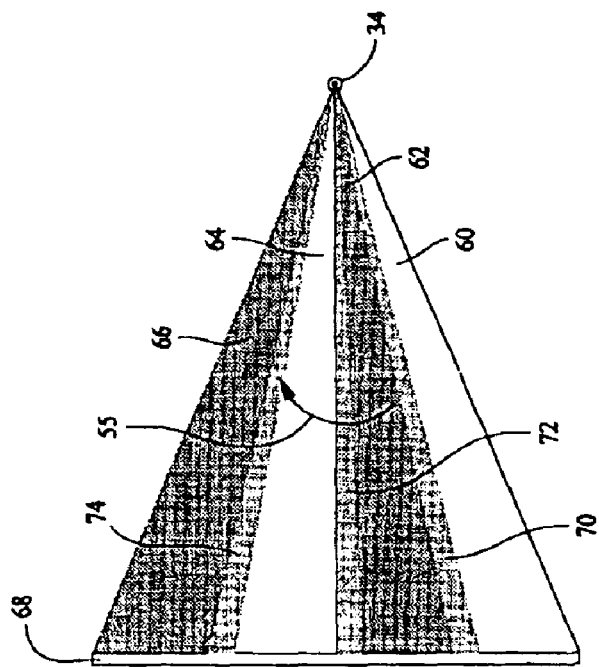
FIG. 3 is a illustration of multiple x-ray fan beams projecting from a focal point of the imaging system of FIG. 1.
Figure 3:
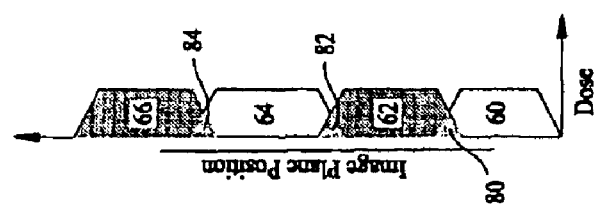

FIG. 3 is a illustration of multiple fan beams projecting from focal point 34. Pasting adjacent images involves taking several images with some overlap as shown in FIG. 3. This can be done in variety of manners from taking straight on images and moving x-ray source 14 and detector array 12 (both of which are not shown in FIG. 3) equal increments in the direction parallel to the image plane, or as in the case of FIG. 3, can be done by angulating collimation assembly 15 (not shown in FIG. 3), and vertically moving detector array 12 between exposures.

In the exemplary embodiment, x-ray source 14 is stationary and collimator assembly 15 rotates, represented by arrow 55, about focal point 34. Rotation of collimation assembly 15 about focal point 34 can be done during exposure as this will have no effect on image quality since x-ray source 14 is at a constant location and only the collimated area is moving. In one embodiment, detector array 12 adjusts or moves in a plurality of positions to follow rotating x-ray beam 16, thereby receiving a plurality of images from x-ray beam 16. Adjustment of detector array 12 in a plurality of positions to receive x-ray beam 16 includes substantially perpendicular positions to x-ray beam 16 (such as position 50 in FIG. 2) and substantially non-perpendicular positions to x-ray beam 16 (such as position 52 in FIG. 2). In a further embodiment, x-ray beam 16 turns off between exposures while collimator assembly 15 rotates about focal point 34.

Thus, detector array 12 receives an image, x-ray beam 16 turns off detector array 12 adjusts to a new position and stops in preparation of receiving the moving x-ray beam 16 in the new position, and x-ray beam 16 turns on again thereby exposing another image on detector array 12. This process repeats until the desired patient coverage is achieved. Finally the plurality of images are then combined or pasted together to form one larger image that is greater in size than detector array 12.

In use, focal point 34 projects a first fan beam 60, a second fan beam 62, a third fan beam 64, and a fourth fan beam 66 at an image plane 68 of detector array 12 (not shown in FIG. 3). A first region 70, a second region 72, and a third region 74 are representative of when x-ray beam 16 is turned off and collimation assembly 15 is rotating about focal point 34. A graph of Image Plane Position versus Dose correlates with first, second, third, and fourth fan beams 60, 62, 64, and 66 and represents the dose for each individual raw image given from first, second, third, and fourth fan beams 60, 62, 64, and 66.

The trapezoidal shape of the doses is due to collimator assembly 15 moving during the exposure, so the areas on the extremes of the image receive less dose as they are either exposed only at the beginning or only at the end. However, the middle portion of the dose trapezoidal profile is constant. A first triangle 80, a second triangle 82, and a third triangle 84 located between trapezoids are the overlap regions shared between images. The collimated area movement for the single image produces a non-uniform dose on the patient, as the extremes of the image would be a linear ramp dose. In one embodiment, overlap regions of first, second, and third triangle 80, 82, and 84 are combined or added together to produce a uniform image. If the next exposure is then started at this "dose-ramp" area, the overlap area is used to locate the proper place for pasting, and the patient receives a uniform dose level at all positions.

The above-described imaging system improves the uniformity of the image quality and the dose given to the patient, as well as providing a simpler positioning profile, resulting in a superior application of dose. In addition, the above described imaging system allows pasting multiple images together into a larger image without double dosing the patient in the overlap regions. In addition it makes the trajectory of the rotating collimator simpler which has the added benefit of less source vibration that can cause blurring in the image.

Exemplary embodiments of an image system assembly are described above in detail. The assemblies are not limited to the specific embodiments described herein, but rather, components of each assembly may be utilized independently and separately from other components described herein. Each image system assembly component can also be used in combination with image and receptor components.

Additionally, although described in the context of a medical setting it is contemplated that the benefits of the invention accrue to non-medical settings, such as, for example, but not limited to, a baggage scanning system typically used in a transportation center, such as, for example, but not limited to, an airport or a rail station.

While the invention has been described in terms of various specific embodiments, those skilled in the art will recognize that the invention can be practiced with modification within the spirit and scope of the claims.

What is claimed is:

1. A method for producing an image in a an X-ray imaging system, the X-ray imaging system including an X-ray source which projects an X-ray beam collimated by a collimation assembly to pass through an object and impinge on an X-ray receptor to produce the image, said method comprising:

rotating the collimation assembly about a focal point while the X-ray source is substantially fixed and producing x-rays; and adjusting the position of the X-ray receptor during rotation of the collimation assembly to receive the X-ray beam in a plurality of positions including a substantially perpendicular position to the X-ray beam and a substantially non-perpendicular position to the X-ray beam.

2. A method according to claim 1 further comprising combining the plurality of images to form one image larger than the X-ray receptor.

3. A method according to claim 2 further comprising adding overlap regions shared between adjacent images together to produce a uniform image.

4. A method according to claim 1 further comprising switching the X-ray beam off between exposures during rotation of the collimation assembly.

5. A method according to claim 1 further comprising producing a digital image from the received X-ray beam.

6. An X-ray imaging system comprising:

an X-ray source configured to produce an X-ray beam;

a collimation assembly rotatably mounted to said X-ray source, said collimation assembly configured to collimate said X-ray beam to pass through an object;

an x-ray receptor wherein said X-ray receptor is adjustable to receive said X-ray beam in a plurality of positions including a substantially non-perpendicular position to said X-ray beam; and a computer operationally coupled to said collimation assembly and said x-ray receptor, said computer configured rotate the collimation assembly about a focal point while the x-ray source is substantially fixed and producing x-rays.

7. An X-ray imaging system according to claim 6 wherein said plurality of images are combined to form one image larger than said X-ray receptor.

8. An X-ray imaging system according to claim 7 wherein said plurality of images having overlap regions between adjacent images, said overlap regions are added together to produce a uniform image.

9. A An X-ray to imaging system according claim 6 wherein said X-ray source switches said X-ray beam off between exposures during rotation of said collimation assembly.

10. An X-ray imaging system according to claim 6 wherein said X-ray receptor is adjustable to receive said X-ray beam in a plurality of positions including a substantially perpendicular position to said X-ray beam.

11. An X-ray imaging system according to claim 6 wherein said X-ray receptor produces a plurality of digital images.

12. A method for producing an image in a medical X-ray imaging system, the medical X-ray imaging system including an X-ray source which projects an X-ray beam collimated by a collimation assembly to pass through an object and impinge on an X-ray receptor to produce the image, said method comprises:

rotating the collimation assembly about a focal point while the X-ray source is substantially fixed to produce a plurality of images; and adjusting the position of the X-ray receptor during rotation of tile collimation assembly to receive the X-ray beam in a plurality of positions including a substantially non-perpendicular position to the X-ray beam.

13. A method according to claim 12 further comprising combining the plurality of images to form one image larger then the X-ray receptor.

14. A method according to claim 13 further comprising adding overlap regions shared between adjacent images together to produce a uniform image.

15. A method according to claim 12 further comprising switching the X-ray beam off between exposures during rotation of the collimation assembly.

16. A method according to claim 12 wherein adjusting the position of the X-ray receptor to receive the X-ray beam in a plurality of positions comprises adjusting the position of the X-ray receptor to receive the X-ray beam in a plurality of positions including a substantially perpendicular position to the X-ray beam.

17. A method according to claim 12 comprising producing a digital image from the received X-ray beam.

18. A computer configured to:

rotate a collimation assembly about a focal point while an X-ray source is substantially fixed and producing x-rays, the X-ray source projecting an X-ray beam collimated by the collimation assembly to pass through an object and impinge on an X-ray receptor to produce a plurality of images; and adjust the position of the X-ray receptor to receive the X-ray beam in a plurality of positions including a substantially non-perpendicular position to said X-ray beam.

19. A computer according to claim 18 further configured to:

switch the X-ray beam off between exposures rotation collimation assembly.

20. A computer according to claim 18 wherein said X-ray receptor is adjustable to receive said X-ray beam in a plurality of positions including a substantially perpendicular position to said X-ray beam.

21. A computer according to claim 18 wherein said X-ray receptor produces a plurality of digital images.

22. A computer readable medium embedded with a program configured to instruct a computer to:

rotate a collimation assembly about a focal point while an X-ray source is substantially fixed and producing x-rays, the X-ray source projects an X-ray beam collimated by the collimation assembly to pass through an object and impinge on an X-ray receptor to produce a plurality of images; and adjust the position of the X-ray receptor to receive the X-ray beam in a plurality of positions including a substantially non-perpendicular position to said X-ray beam.

23. A computer readable medium embedded with the program configured to instruct the computer according to claim 22 further configured to combine the plurality of images to form one image larger than the X-ray receptor.

24. A computer readable medium embedded with the program configured to instruct the computer according to claim 23 further configured to add overlapping regions shared between adjacent images together to produce a uniform image.

* * * * *

UNITED STATES PATENT AND TRADEMARK OFFICE
CERTIFICATE OF CORRECTION

PATENT NO. : 6,898,269 B2  Page 1 of 1
APPLICATION NO. : 10/248698
DATED : May 24, 2005
INVENTOR(S) : Halsmer et al.

It is certified that error appears in the above-identified patent and that said Letters Patent is hereby corrected as shown below:

In Claim 1, column 4, line 65, delete "in a an X-ray" and insert therefor -- in an X-ray --.

In Claim 6, column 5, line 29, between "receptor" and "wherein" insert -- , --.

In Claim 9, column 5, line 45, delete "A An X-ray to imaging" and insert therefor -- An X-ray imaging --.

In Claim 9, column 5, line 45, between "according" and "claim" insert -- to --.

In Claim 12, column 6, line 2, delete "tile" and insert therefor -- the --.

In Claim 13, column 6, line 7, delete "then" and insert therefor -- than --.

In Claim 17, column 6, line 20, between "12" and "comprising" insert -- further --.

In Claim 19, column 6, line 35, between "exposures" and "rotation" insert -- during --.

In Claim 19, column 6, line 36, between "rotation" and "collimation" insert -- of the --.

Signed and Sealed this

Fourth Day of December, 2007

JON W. DUDAS
*Director of the United States Patent and Trademark Office*